US006555122B2

United States Patent
Lo et al.

(10) Patent No.: US 6,555,122 B2
(45) Date of Patent: *Apr. 29, 2003

(54) DRY WATER-DISPERSIBLE COMPOSITIONS OF MICROENCAPSULATED PESTICIDES

(75) Inventors: Ray Jia Ruey Lo, Alameda, CA (US); Jin Ling Chen, Randolph, NJ (US); Herbert Benson Scher, Moraga, CA (US); Juanita Elena Van Koppenhagen, Vallejo, CA (US); Ian Malcolm Shirley, Binfield (GB)

(73) Assignee: Syngenta Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/113,722

(22) Filed: May 13, 2002

(65) Prior Publication Data

US 2002/0164363 A1 Nov. 7, 2002

Related U.S. Application Data

(63) Continuation of application No. 09/572,515, filed on May 17, 2000, now Pat. No. 6,419,942, which is a continuation of application No. 09/118,513, filed on Jul. 17, 1998, now Pat. No. 6,358,520, which is a continuation of application No. 08/476,540, filed on Jun. 7, 1995, now abandoned.

(51) Int. Cl.[7] .............................................. A01N 25/28

(52) U.S. Cl. ...................... 424/408; 424/405; 424/406; 424/409; 424/417; 424/419; 424/485; 424/487; 514/531

(58) Field of Search ................................. 424/405, 408, 424/409, 417, 484–490, 497, 406, 418–420, 421; 514/521, 531

(56) References Cited

U.S. PATENT DOCUMENTS

| 3,429,827 | A |   | 2/1969  | Ruus ........................... 252/316 |
|-----------|---|---|---------|-----------------------------------------|
| 4,244,836 | A |   | 1/1981  | Frensch et al. .............. 252/316    |
| 4,532,123 | A |   | 7/1985  | Gardner ........................ 424/21  |
| 4,696,822 | A |   | 9/1987  | Matsumura et al. ......... 424/490       |
| 4,891,172 | A |   | 1/1990  | Matsushita et al. ......... 264/4.33     |
| 4,936,901 | A |   | 6/1990  | Surgant, Sr. et al. ............ 71/92   |
| 5,160,530 | A |   | 11/1992 | Misselbrook et al. ......... 71/121      |
| 5,354,742 | A |   | 10/1994 | Deming et al. .............. 514/117     |
| 5,470,512 | A | * | 11/1995 | Noji et al. .................... 264/4.1 |
| 5,576,008 | A |   | 11/1996 | Yang et al. ................. 424/408    |
| 6,077,522 | A |   | 6/2000  | Scher et al. ................. 424/408   |
| 6,419,942 | B1| * | 7/2002  | Lo et al. ..................... 424/408  |

* cited by examiner

Primary Examiner—Neil S. Levy
(74) Attorney, Agent, or Firm—William A. Teoli, Jr.; Thomas Hamilton

(57) ABSTRACT

Solid water-dispersible compositions containing microencapsulated pesticides are produced by spray-drying an aqueous suspension of said pesticides in the presence of a water-soluble polymer.

12 Claims, 2 Drawing Sheets

DRY WATER-DISPERSIBLE COMPOSITIONS OF MICROENCAPSULATED PESTICIDES

RELATED APPLICATIONS

The present application is a continuation of application Ser. No. 09/572,515 filed May 17, 2000, issued as U.S. Pat. No. 6,419,942, which is a continuation of application Ser. No. 09/118,513 filed on Jul. 17, 1998, issued as U.S. Pat. No. 6,358,520, which is a continuation of application Ser. No. 08/476,540 filed on Jun. 7, 1995 abandoned.

FIELD OF THE INVENTION

This invention relates to production of dry water-dispersible compositions containing microencapsulated pesticides.

BACKGROUND OF THE INVENTION

Microencapsulation is one of the techniques or methods utilized in producing pesticidal compositions, and is particularly useful in producing compositions containing low-melting solid pesticides. For the most part, microencapsulation of pesticides is utilized when a slow or controlled release of the pesticide is desired. This is accomplished by encapsulating particles or droplets of a material containing a pesticide within a polymeric shell through which the pesticide migrates at a controlled rate. The rate of release of the pesticide is determined by both the nature of the pesticide and by the type, structure and properties of the capsule shell. The nature of the shell, in turn, can be predetermined or constructed, as is known in the art, by selection of the type and quantity of polymer and the conditions under which the shell wall is formed.

Microencapsulated formulations or compositions have a number of additional advantages relating to safety and toxicity. Since the pesticide is contained within a polymeric wall, there is in general less dusting and much lower toxicity associated with the production, handling and application of pesticides so formulated, as well as lower animal toxicity.

It is also possible to produce microencapsulated formulations of pesticides in which controlled release is not the objective. Such compositions contain the pesticide in microcapsules which are generally on the smaller side, and tend to have relatively thin walls. Microencapsulated pesticides of this type would be intended for certain foliar applications, in situations in which a relatively quick release of the entire contents of the microcapsules is desired. However, even though controlled release may not be an objective, it is nevertheless desirable to take advantage of the lessened toxicity and dust formation of microencapsulated pesticides as compared to non-microencapsulated forms.

Microencapsulated pesticides, whether of the controlled release or the quick release variety, are usually sold in the form of aqueous suspensions of the microcapsules. Such suspensions naturally result from the process for the production of microcapsules which in general involves the formation of a dispersion or emulsion of a relatively non-water soluble liquid ("oil") in an aqueous medium. The oil phase contains a pesticide to be encapsulated as well as one or more monomers which will form the polymeric microcapsule wall. The microencapsulated products are produced by forming the oil/water dispersion, followed by heating and other means to produce polymerization, resulting in polymeric microcapsules containing the non-water soluble liquid material, suspended in the aqueous phase.

In general, it would be further advantageous to provide such microencapsulated compositions in dry form, rather than as aqueous suspensions. Dry formulations may be prepared with relatively high loading of the pesticide, are easier to remove from containers, produce less contamination in the environment, may be stored for long periods of time, and their storage and transportation does not require the simultaneous storage and transport of large volumes of water. In addition, since pesticidal microcapsules are typically applied by dilution of the microencapsulated formulation with water in a spray tank to form a sprayable emulsion, it would be convenient to provide a solid formulation of microencapsulated pesticides which is water dispersible, i.e., can easily be mixed with water to produce such a sprayable material.

SUMMARY OF THE INVENTION

In one aspect, this invention comprises a process for the production of a water-dispersible composition containing a microencapsulated pesticide, said process comprising (a) preparing an aqueous suspension comprising microcapsules containing at least one water-insoluble pesticide enclosed within a polymeric shell suspended in an aqueous medium containing a water-soluble polymer; and (b) spray-drying the aqueous suspension of step (a) to produce a water-dispersible composition comprising said microcapsules in a matrix comprising the water-soluble polymer, wherein the water-soluble polymer comprises from about 4 to about 15 weight percent of the water-dispersible composition.

A second aspect of the invention comprises the products thus prepared, which comprise microcapsules containing at least one water-insoluble pesticide within a polymeric shell, the microcapsules being contained within a matrix comprising a water-soluble polymer, the water-soluble polymer comprising from about 4 to about 15 weight percent of the water-dispersible composition.

DETAILED DESCRIPTION OF THE INVENTION

Figure 1:
FIG. 1 is an electron micrograph showing a typical dispersible composition of this invention.

According to this invention, there are prepared relatively dry water-dispersible compositions of a granular nature in the form of matrix particles of a water-soluble polymer which contain within the matrix microcapsules of a polymeric shell which in turn contain one or more water-insoluble pesticides. In brief, these compositions are prepared by spray drying an aqueous suspension of a microencapsulated pesticide in the presence of a water-soluble polymer. The amount of water-soluble polymer utilized in the spray drying is an amount which will provide from about 4 to about 15 weight percent of the water-soluble polymer in the spray-dried product.

Microcapsules containing pesticides usable in this invention may be prepared by any of the known microencapsulation techniques. However, they are preferably prepared by interfacial polymerization processes. In these processes, a relatively water-insoluble (generally termed an "organic" or "oil") liquid phase is prepared which contains one or more liquid pesticides, or one or more liquid or solid pesticides dissolved or suspended in a solvent, optionally one or more surfactants and one or more monomers which will become polymerized to form a polymeric shell for the capsule. The organic phase is then added to an aqueous phase with agitation, forming a dispersion or emulsion of organic (discontinuous) phase droplets in the aqueous (continuous) phase. The aqueous phase may contain one or more surfactants, protective colloids, and other ingredients as known in the art. The dispersion is then subjected to conditions (usually agitation and heating) so as to cause the monomer or monomers contained in the organic phase droplets to polymerize at the interface between the organic and aqueous phases, forming shells of polymer around the droplets. The result is a suspension of microcapsules in the aqueous phase.

A process for production of relatively dry water-dispersible compositions of microencapsulated pesticides is described in U.S. Pat. No. 5,354,742. In that process, typical spray drying adjuvants are then added to such an aqueous suspension of microcapsules, and the resulting suspension is spray dried as described therein to produce water-dispersible granules containing the microcapsules. The spray-drying adjuvants (also referred to as "suspension adjuvants", "agglomeration adjuvants" and "formulation adjuvants") are preferably water-soluble salts such as ammonium sulfate or sodium, potassium or calcium chlorides. The adjuvants may also include surfactants, water soluble polymers, higher alcohols and other water-soluble or water-dispersible components such as gums, clays and silicas. No ranges are given in the patent for the amount or amounts of such adjuvants utilized in the process. Among the additional adjuvants are included water-soluble polymers such as polyvinyl pyrrolidone (PVP) and polyvinyl alcohol (PVA) electrolytes. The only example in which any such material used is Example 8 in which the microcapsule suspension contains 0.49 weight percent PVP. According to the patent the formulation adjuvants function to cause agglomeration of microcapsules during the spray drying; as water is removed from each droplet emanating from the spray nozzle, an aggregate is formed containing many small microcapsules associated together with a fine layer of adjuvant homogenously interspersed between each microcapsule. The adjuvant thus functions by both separating the microcapsules from each other and bridging the capsules to each other, thus producing agglomeration of the capsules into larger granules which are dispersible in water.

However, it has been found that a technique of this type is not suitable for producing water-dispersible granules or agglomerated compositions of pesticidal microcapsules having relatively small particle size and relatively thin walls. Attempts to produce dispersible materials from such microcapsules using the technique of U.S. Pat. No. 5,354,742 resulted in a sticky material which could not be dispersed in water.

The water soluble polymers usable in this invention include both synthetic and natural polymers such as polyvinylpyrrolidone, polyvinyl alcohol, polyethylene oxides, ethylene/maleic anhydride copolymer, methyl vinyl ether-maleic anhydride copolymer, water-soluble cellulose, water-soluble polyamides or polyesters, copolymers or homopolymers of acrylic acids, water-soluble starches and modified starches, natural gums such as alginates, dextrins and proteins such as gelatins and caseins. Preferably the water-soluble polymer is polyvinyl alcohol.

Polyvinyl alcohol is usually sold in solid form, in a number of variations of molecular weight and degree of hydrolysis. In general, polyvinyl alcohol of lower molecular weight or lesser degree of hydrolysis tends to be more water-soluble, and thus is more preferred. For instance, partially hydrolyzed polyvinyl alcohols (e.g., up to about 89–90% hydrolyzed) tend to be more water soluble and thus preferred for use in this invention.

For example, of the Airvol line of polyvinyl alcohols available from Air Products & Chemicals, Inc., the preferred polyvinyl alcohol is Airvol 203. It is 87–89% hydrolyzed, may be dissolved in water to form solutions of up to 30% PVA by weight, and has a viscosity of 3.5–4.5 cps (4% aqueous solution, 20° C.). Two other products, Airvol 103 and 107, have a higher degree of hydrolysis (98–98.8%) but a lower molecular weight. They would also be suitable for use in the present invention but products produced from them would tend to disperse more slowly in water.

The solid polyvinyl alcohols are used in this invention by dissolving them in water to form solutions.

It may be advantageous to include some water-soluble polymer in the process in which the microcapsules are formed, as polyvinyl alcohol and some other polymers are known to be useful, for instance, as protective colloids or co-surfactants to enhance the stability of the oil-in-water emulsion. However, the amount of water-soluble polymer for this purpose should be kept relatively low, preferably about 5 weight % or less, more preferably no more than 2–3 weight percent. Thus, if the amount of water-soluble polymer utilized is toward the lower end of the range of this invention, i.e., about 4–5% by weight, the water-soluble polymer may either be added to the suspension of microcapsules after the microcapsules have been formed, or may be initially added in the aqueous phase during the formation of the dispersion and the resulting microcapsules. However, if the amount of water-soluble polymer utilized is toward the higher end (from about 5 to about 15 weight percent) or is a more viscous material, it must be added to an already prepared suspension of microcapsules, and should not be present in the microcapsule production process, as it may be too viscous for good emulsion to form or may interfere with the production of the capsule shell walls.

If the concentration of pesticide is relatively low, the microencapsulation process may be able to tolerate higher amounts of water-soluble polymer up to about 10%.

The amount of water-soluble polymer utilized in this invention is that which will result in a water-dispersible product containing from about 4 to about 15 weight percent water-soluble polymer. As will be discussed below, the water-dispersible product contains polymeric microcapsules (which contain a liquid material including one or more pesticides and optionally one or more solvents and/or surfactants), the water-soluble polymer, and optionally spray-drying adjuvants.

The organic phase (i.e., the encapsulated material) may contain any suitable pesticide or pesticides, whether liquid or solid. The pesticide may be utilized per se when a liquid, or may be dissolved or suspended in an appropriate solvent. Also present in the organic phase are one or more monomers which will be caused to become polymerized at the organic/aqueous phase interface to form the polymeric shell of the microcapsules. As mentioned previously, the monomers may be any of those utilized to produce polymeric microcapsules; however, the polymers most suitable for use in this invention are polyureas and urea/formaldehyde copolymers. The polyureas may be produced, as described in U.S. Pat. No. 4,285,720 by condensation of one or more organic polyisocyanates. Alternatively they may be produced as described in U.S. Pat. No. 5,354,742 by reaction between an organic polyisocyanate and an organic amine. The urea/formaldehyde copolymers are produced by self-condensation of etherified amino resins as described in U.S.

Pat. No. 4,956,129. However, other known types of microcapsules such as polyamides, polyesters, polyurethanes and polycarbonates, may be utilized in the process of this invention.

The organic phase and consequently the encapsulated liquid may, in addition to the pesticide and solvent, also contain one or more surfactants and may additionally contain a suspended particulate well-dispersed ultraviolet protectant material such as titanium dioxide and/or zinc oxide in the event that the pesticide is sensitive to ultraviolet light. Production of microcapsules containing such suspended ultraviolet light protectants is described in co-pending U.S. patent application Ser. No. 08/430,030, filed Apr. 27, 1995, in which two of us are named as inventors.

The process of this invention may be utilized to produce water-dispersible compositions in which the pesticide is any of those suitable for encapsulation, and is particularly useful for producing compositions containing relatively low melting pesticides, particularly insecticidal pyrethroids such as lambda-cyhalothrin, permethrin, cypermethrin, and many others, as well as other low-melting pesticides such as the herbicides napropamide, fluazifop-butyl and its resolved isomer fluazifop-P-butyl and the fungicide azoxystrobin.

The spray drying of the microcapsule is carried out under typical spray-drying conditions and with the use of typical spray-drying equipment in which the inlet temperatures generally range from about 105 to about 200° C. and output temperatures range from about 45 to about 95° C.

It may also be advantageous to add to the microcapsule suspension prior to conducting the spray drying, typical spray drying adjuvants or additives such as clays, gums, surfactants, etc. as these may in general improve the spray drying procedure and the product quality obtained therefrom.

The process of the present invention is suitable for preparing water-dispersible compositions of microcapsules of both the relatively thin-walled quick-release type and the relatively thicker-walled controlled-release type. However, it is particularly suitable for producing dispersions of the relatively thin-walled type of microcapsules.

The products produced by the process of this invention are in the form of a matrix of the water-soluble polymer (e.g., polyvinyl alcohol) containing the microcapsules. The products thus have a double barrier preventing release of the active ingredient—the polymeric shell of the capsule which is essentially surrounded by a hydrophilic polymer which serves to maintain the active ingredient within the capsule shell walls as well as protecting the shell from being adversely affected by the surrounding conditions.

EXAMPLES

The following are representative examples of the conduct of this invention.

The following general procedure was employed in conducting Examples 1–6: A suspension of microcapsules containing lambda-cyhalothrin was prepared as generally described in U.S. Pat. No. 4,285,720, in which the active material is encapsulated within a polyurea shell wall formed by interfacial polymerization and condensation of a mixture of isomers of toluene diisocyanate and polymethylene polyphenyl isocyanate (PAPI). The product was an aqueous suspension of microcapsules in which the microcapsules had an average particle size of about 3 microns and a wall content of about 7.5 weight percent (based on the oil phase). In some examples the lambda-cyhalothrin was dissolved in a solvent (usually Solvesso 200 aromatic solvent, obtained from Exxon); in others no solvent was used and the lambda-cyhalothrin was encapsulated in molten form. In Example 2, the microcapsules also included 4.2 weight percent titanium dioxide suspended and dispersed throughout the liquid phase within the microcapsules. Microcapsules of this type were prepared as described in co-pending application Ser. No. 08/430,030, filed Apr. 27, 1995.

The microcapsule suspension was gently mixed with the indicated amount of polyvinyl alcohol solution at 500 rpm for five minutes. The resulting suspension was filtered through a 100 mesh screen and spray-dried at an inlet temperature of 150±10° C. and an outlet temperature of 70±10° C.

The polyvinyl alcohol utilized in these examples was Airvol 203, obtained from Air Products and Chemicals, Inc. It is 87–89% hydrolyzed and has a pH of 4.5–6.5.

Example 1

A composition was prepared according to the foregoing procedure, in which lambda-cyhalothrin dissolved in Solvesso 200 aromatic solvent (Exxon) was microencapsulated. Spray dry adjuvants added were Reax 85A lignosulfonate (3.03 weight % of dry product), Kelzan xanthan gum (0.25 weight %), and Witconate 90 surfactant (0.48 weight %). After spray drying the product contained 45.6 weight percent lambda-cyhalothrin and 10.3 weight percent polyvinyl alcohol. The dispersible product had a particle size range of approximately 20–80 microns.

Example 2

A product similar to that in Example 1 was prepared, containing approximately 42.0 weight percent lambda-cyhalothrin, 9.5 weight percent polyvinyl alcohol, and 4.2 weight percent titanium dioxide. The dispersible product had a particle size range of about 20–80 microns.

Examples 3–6

Compositions were prepared by the above method including ingredients as listed below in Table 1. The compositions were tested for dispersibility by placing 0.042 grams of the composition in a graduated cylinder containing 100 mL water and inverting the cylinder until the material was completely dispersed. Table 1 indicates the number of inversions of each composition necessary to achieve this state, and also shows the pH of each composition thus prepared. Some compositions included other spray-drying adjuvants such as Colloid 225 and Soprophor FLK surfactant.

The compositions of Examples 3–6 were tested for storage stability at temperatures of −10° C., +40° C. and +50° C. for up to twelve weeks and demonstrated good thermal stability in these tests. The compositions were also tested for biological activity against two strains of the tobacco budworm (*Heliothis virescens*)—a pyrethroid resistant strain (PEG-87) and a pyrethriod susceptible strain (BRC). $LC_{50}$ values were obtained ranging from 0.18–0.34 ppm for the susceptible strain and 109–241 ppm for the resistant strain.

TABLE I

|  | Example: | | | |
|---|---|---|---|---|
| Weight % | 3 | 4 | 5 | 6 |
| lambda-cyhalothrin | 47.1 | 47.6 | 46.8 | 44.6 |
| PVA | 12.7 | 5.4 | 9.7 | 9.9 |
| Reax 85A | 2.9 | — | — | 2.9 |
| Kaolin | — | 6.2 | — | — |
| Colloid 255 | — | 5.4 | — | — |
| Witconate AOK | — | 0.8 | — | — |
| Soprophor FLK | — | — | 4.8 | — |

TABLE I-continued

| Weight % | Example: 3 | 4 | 5 | 6 |
|---|---|---|---|---|
| Other ingredients* | 37.3 | 34.6 | 38.7 | 42.6 |
| Dispersibiity (# inversions) | 20 | 30 | 36 | 20 |
| pH | 5.0 | 7.9 | 5.0 | 5.0 |

*Includes microcapsule shell wall, solvents and other ingredients used in producing the microcapsules.

Example 7

Microcapsules were prepared as before, but containing as the active ingredient technical grade fluazifop-butyl (44.8 weight percent in the aqueous suspension). There were then added, as spray drying adjuvants, soda ash (0.48 weight percent) Kelzan xanthan gum (0.09 weight percent) 50% caustic solution (0.08 weight percent) and also Proxel GXL biocide (0.09 weight percent). There was then added 13.53 grams of polyvinyl alcohol (Airvol 203, 20% aqueous solution). Spray drying as before produced a dispersible composition.

Figure 2:
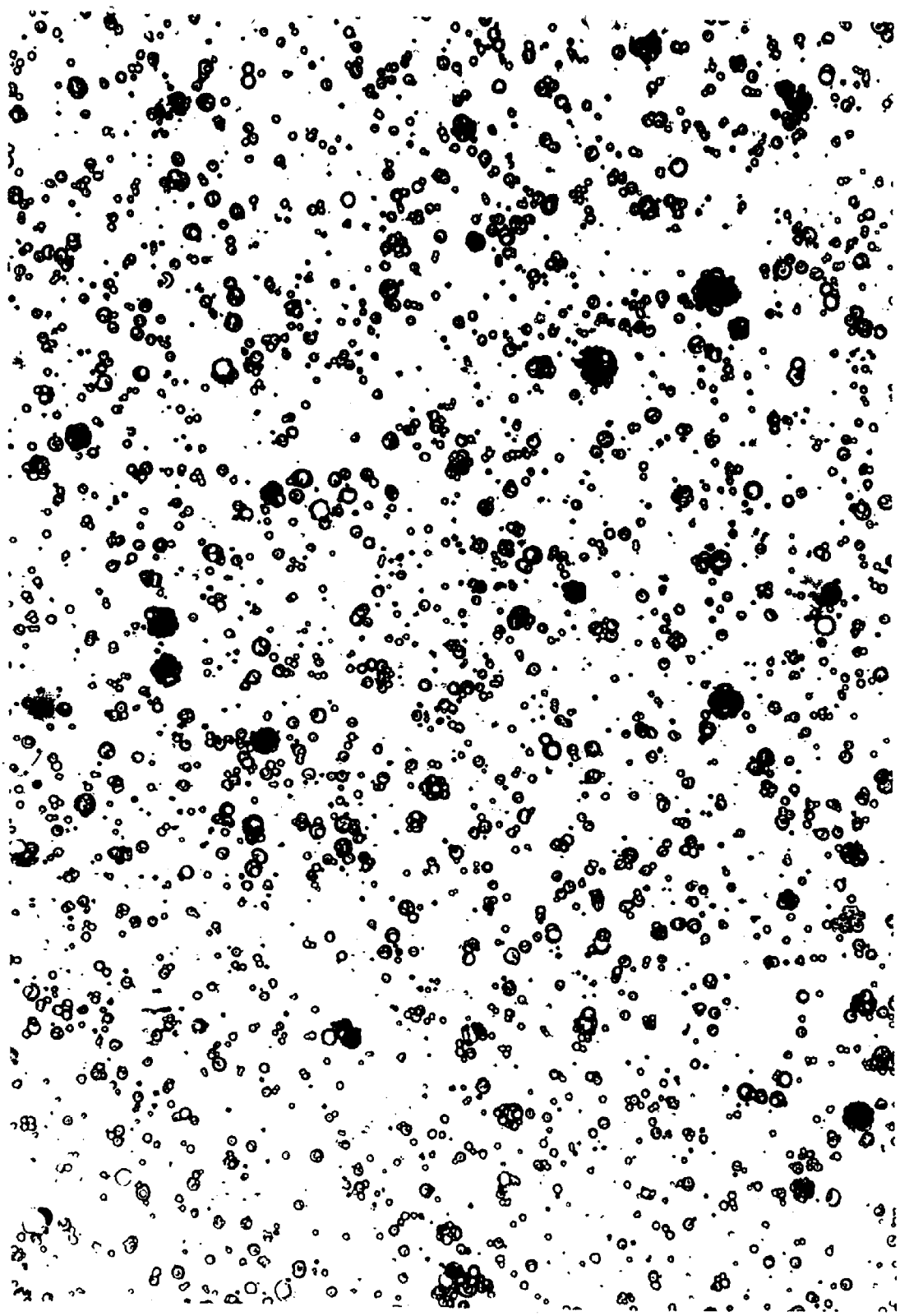
FIG. 2 is a micrograph showing the dispersion of microcapsules from a typical dispersible product of this invention.

FIG. 1 is an electron micrograph (2000×) of a typical water-dispersible product showing the agglomeration of microcapsules in matrixes of polyvinyl alcohol. FIG. 2 is a micrograph (600×) of such a product after dispersion in water, and clearly shows that nearly all the large materials have dissolved and the microcapsules have been well dispersed.

What is claimed is:

1. A water dispersible composition comprising microcapsules wherein each microcapsule comprises
   (a) a core comprising at least one water-insoluble pesticide within
   (b) a polymeric shell comprising a polyurea or a urea/formaldehyde copolymer,
   said microcapsules being contained within a matrix comprising one or more water-soluble polymers wherein said one or more water-soluble polymers are present in an amount of from about 4 to about 15 weight percent of said water-dispersible composition and in which at least one of said water-soluble polymers is a copolymer or homopolymer of acrylic acid.

2. The composition of claim 1, wherein said one or more water-soluble polymers is present in an amount of from about 4 to about 10 percent of said water dispersible composition.

3. The composition of claim 1, wherein said water-dispersible composition further comprises one or more spray-drying adjuvants.

4. The composition of claim 1, wherein said water-soluble polymers further comprise at least one member selected from the group consisting of a polyvinylpyrrolidone, a polyvinyl alcohol, a polyethylene oxide, an ethylene/maleic anhydride copolymer, a methyl vinyl ether maleic anhydride copolymer, a water-soluble cellulose, a water-soluble polyamide, a water-soluble polyester, a water-soluble starch and a modified starch, gum, dextrin and a water-soluble protein.

5. The composition of claim 1, wherein the pesticide is a pyrethroid, a napropamide, a fluazifop-butyl, a fluazifop-P-butyl, an azoxystrobin, or a mixture thereof.

6. The composition of claim 1, wherein the pesticide is lambda-cyhalothrin, permethrin, or cypermethrin.

7. The composition of claim 6, wherein the pesticide is lambda-cyhalothrin.

8. The composition of claim 1, wherein the microcapsule cores comprise a solid material suspended within a liquid material.

9. The composition of claim 8, wherein the solid material and liquid material are both pesticides.

10. The composition of claim 8, wherein the solid material is an ultraviolet light protectant thoroughly dispersed in the liquid as a particulate.

11. The composition of claim 1, wherein the microcapsule core further comprises one or more surfactants, one or more solvents, or a mixture thereof.

12. The composition of claim 3, wherein the spray-drying adjuvant is a clay, a gum, a surfactant, or a mixture thereof.

* * * * *